United States Patent [19]
Bilitz et al.

[11] Patent Number: 5,817,104
[45] Date of Patent: Oct. 6, 1998

[54] DUAL PURPOSE MECHANISM FOR EXPANDING BASKETS

[75] Inventors: Mark R. Bilitz, Minneapolis, Minn.; Rance A. Winkler, Atlanta; Larry A. Roberts, Marietta, both of Ga.

[73] Assignee: C.R. Bard, Inc., Murray Hill, N.J.

[21] Appl. No.: 846,915

[22] Filed: Apr. 30, 1997

[51] Int. Cl.$^6$ .................................................. A61B 17/22
[52] U.S. Cl. .......................................... 606/127; 606/113
[58] Field of Search ................................... 606/127, 128, 606/113, 103

[56] References Cited

U.S. PATENT DOCUMENTS

| | | |
|---|---|---|
| 4,256,113 | 3/1981 | Chamness . |
| 4,741,335 | 5/1988 | Okada . |
| 5,171,314 | 12/1992 | Dulebohn . |
| 5,311,858 | 5/1994 | Adair ................................ 606/127 |
| 5,376,094 | 12/1994 | Kline . |
| 5,496,330 | 3/1996 | Bates et al. . |

*Primary Examiner*—Michael Powell Buiz
*Assistant Examiner*—Julian W. Woo
*Attorney, Agent, or Firm*—Jones & Askew, LLP

[57] ABSTRACT

An improved stone basket is disclosed which comprises a handle having a slide and a piston movably mounted to it. In a first embodiment the distal end of a sheath is attached to the slide, and the distal end of a control wire is attached to the piston. A basket shaft is fixedly mounted to the handle. Initial rearward movement of the slide causes the sheath to retract over the fixed basket shaft, exposing a basket member at the forward end of the basket shaft and permitting it to open. Further rearward movement of the slide by the physician brings the slide into driving engagment with the piston. Thereafter, subsequent movement of the slide displaces the piston to exert a tension on the control wire to expand the basket member. In a second embodiment the sheath is fixedly mounted to the forward end of the handle. The rearward end of the basket shaft is mounted to the thumb slide, and the rearward end of the control wire is attached to the piston. A spring operatively associated with the slide and the piston biases the piston forward as the thumb slide is advanced and permits limited forward movement of the thumb slide after the piston reaches the forward extent of its movement. Thereafter the thumb slide can be advanced without advancing the piston, thus extending the basket shaft toward the tip of the basket assembly and expanding the basket.

6 Claims, 10 Drawing Sheets

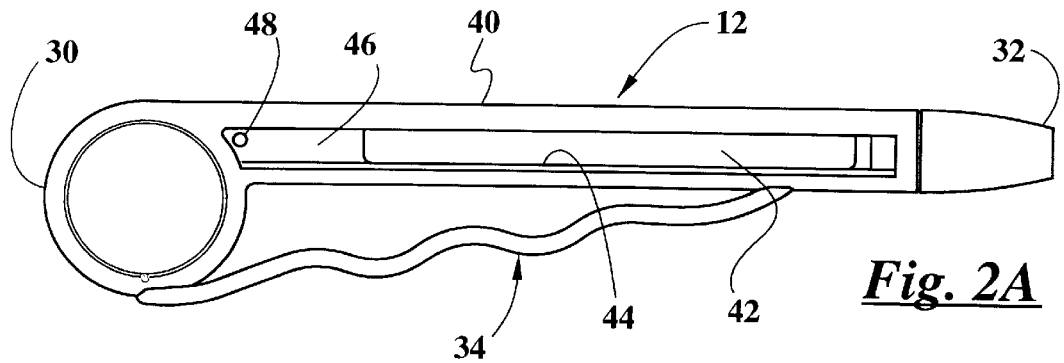
Fig. 2A
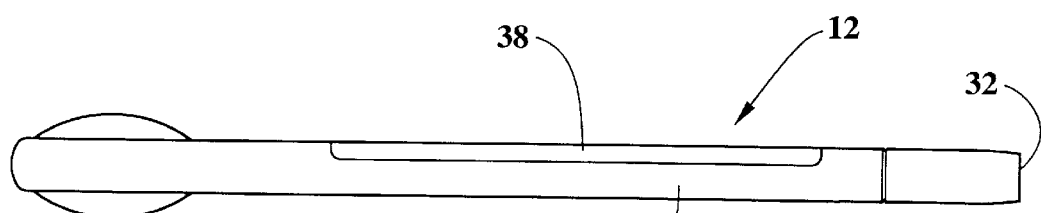
Fig. 2B
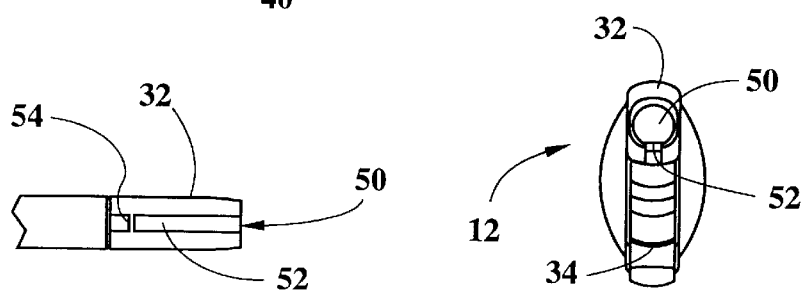
Fig. 2D     Fig. 2C
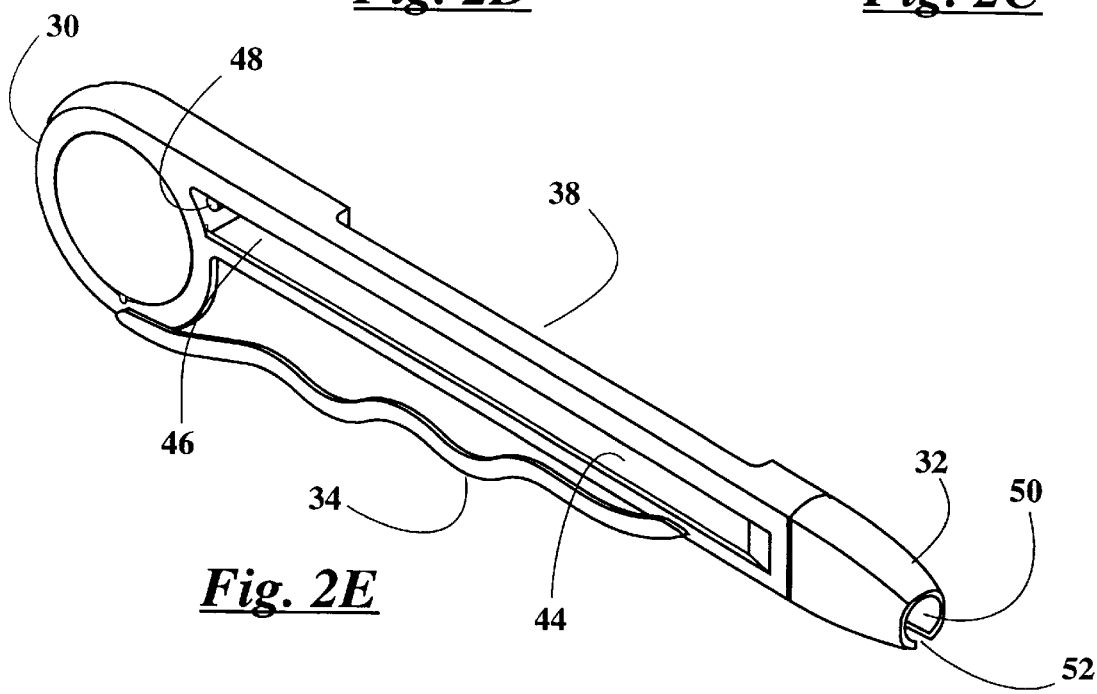
Fig. 2E

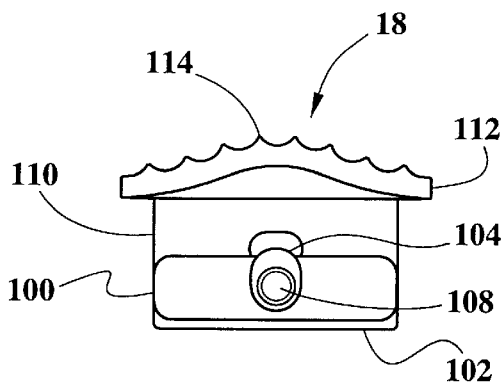
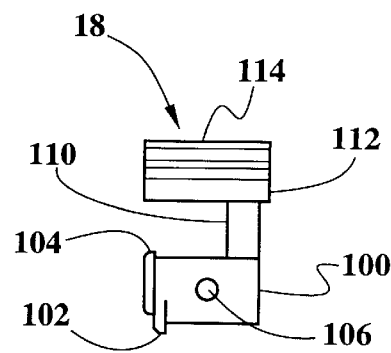
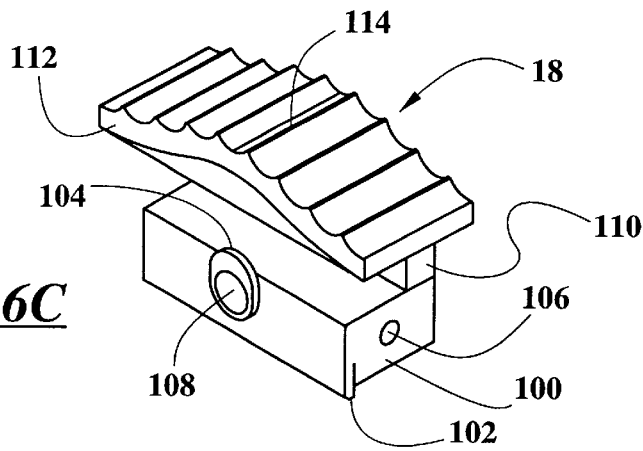
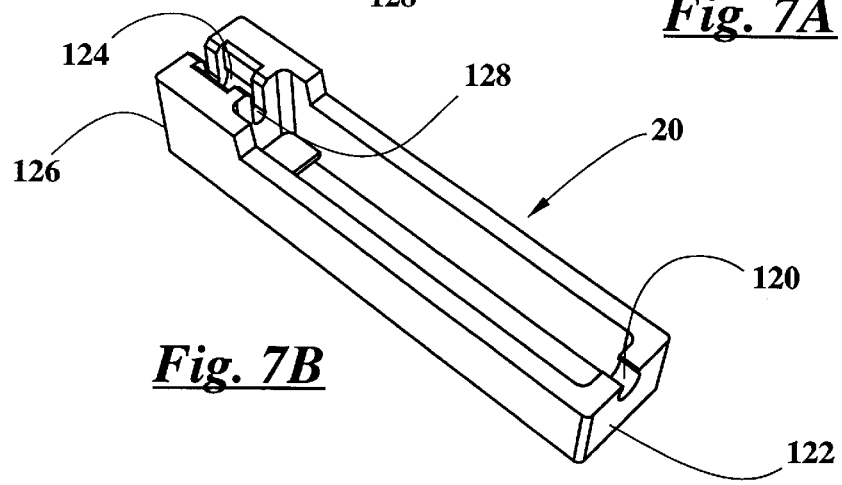

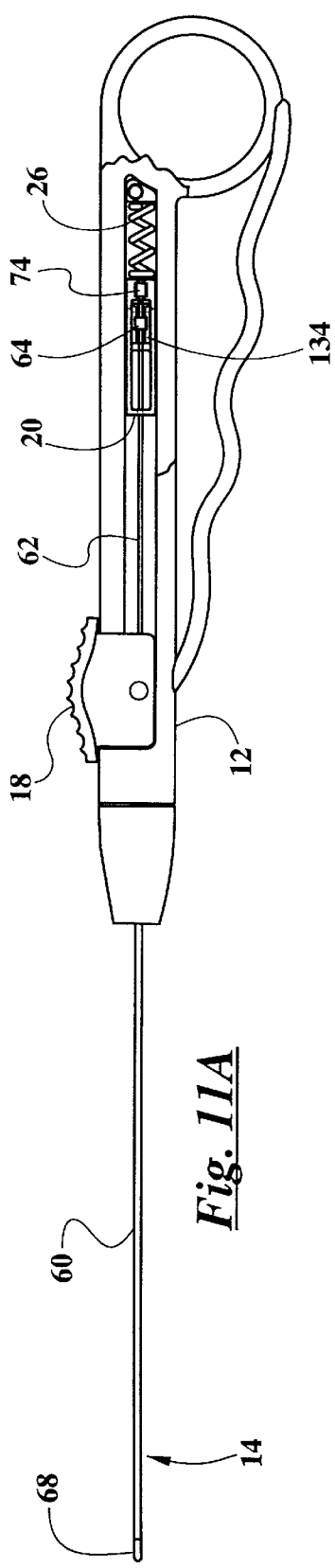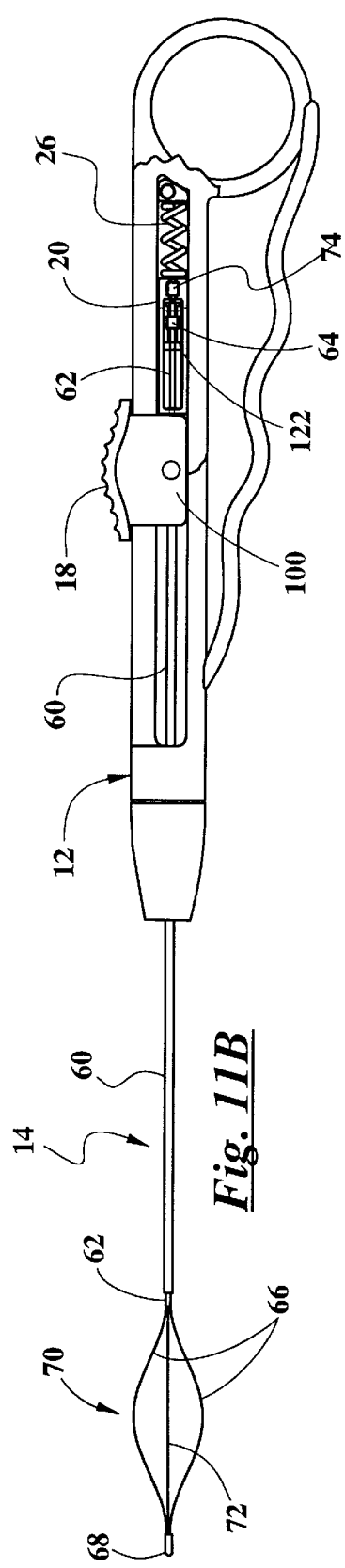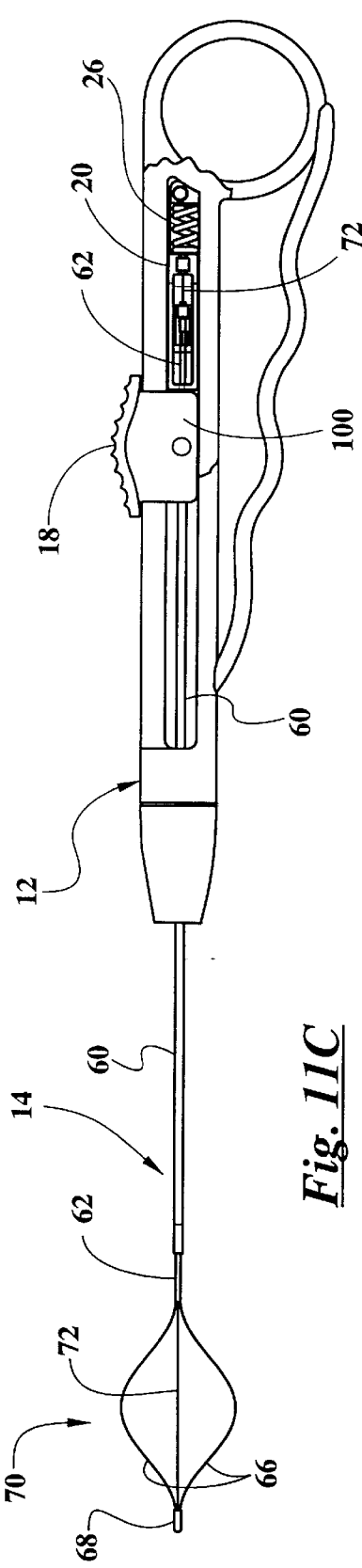

DUAL PURPOSE MECHANISM FOR EXPANDING BASKETS

TECHNICAL FIELD

The present invention relates generally to medical devices and relates more specifically to an expanding stone basket.

BACKGROUND OF THE INVENTION

Expanding stone baskets for removing stones from the human urinary tract are well known. In a conventional stone basket, a helical basket is located at the forward end of a basket tube. A control wire extends through the basket tube and is connected to the forward end of the basket. A sheath is telescopically disposed over the basket tube to facilitate introduction of the instrument into the patient's urinary tract. When the sheath is in its forwardmost position, the basket is concealed within the forward end of the sheath. When the sheath is retracted to expose the basket member, the wires of the basket expand outward. Tension can be exerted on the control wire to draw the forward end of the basket rearward, causing the basket to expand radially outward even further.

The stone basket is inserted through the urethra and advanced through the urinary tract to a location proximate to the stone. The physician then retracts the sheath to expose the stone basket and then exerts a tension on the control wire to expand the basket member. The stone basket is then maneuvered under ultrasound or other suitable visualization until the basket surrounds the stone. The physician then releases the tension on the control wire and then advances the sheath to close the basket member around the stone. When the stone has been captured within the basket, the basket can be closed tightly around the stone to crush it or to grasp it as it is withdrawn from the patient.

To enable the physician to manipulate the stone basket, conventional baskets provide a handle at the distal end of the device. A pair of slides is mounted to the handle. One of the slides is connected to the sheath, and the other slide is connected to the control wire. The physician moves the first slide to retract the sheath and expose the basket. He then moves the second slide to exert a tension on the control wire to expand the basket.

There are various problems associated with conventional expanding stone baskets. One problem is that, to open the basket fully, the physician must actuate two separate slides: the first slide to retract the sheath, and the second slide to retract the control wire. When the physician's attention is focused on an ultrasound monitor to manipulate the basket to capture the stone, having to look down at the handle to locate the appropriate slide is an unwelcome distraction. Thus there is a need for a stone basket which does not require the physician to relocate his finger from one slide to another to expand and to manipulate the basket.

Another problem relates to the fact that the wires comprising the control wire and the basket member must of necessity be of small diameter to provide a basket which will collapse to a minimum diameter, thereby to minimize trauma as the basket is inserted into the patient. Minimizing the diameter of the control wire has an adverse effect on the strength of the wire, such that the control wire cannot withstand excess tension. If the physician exerts a tension on the control wire while the basket is still encased within its sheath, the basket will be prevented from expanding. The likely result is that the control wire will break, thereby rendering the basket inoperative. Thus there is a need for a stone basket in which tension cannot be exerted on the control wire while the basket is still encased within its sheath.

SUMMARY OF THE INVENTION

Stated generally, the present invention comprises an improved stone basket for removing stones from the urinary tract of a human patient. The stone basket of the present invention permits the physician to actuate the sheath and the control wire from a single slide, thereby eliminating the need for the physician to move his finger from one slide to another, and also eliminating the attendant distraction to the physician during a critical phase of the procedure. The stone basket of the present invention also prevents the physician from inadvertently tensioning the center wire while the basket is still enclosed within its sheath, thereby minimizing the possibility of breaking the center wire.

Stated somewhat more specifically, the improved stone basket of the present invention comprises a handle having a slide and a piston movably mounted to it. In a first embodiment the distal end of the sheath is attached to the slide, and the distal end of the control wire is attached to the piston. The basket tube is fixedly mounted to the handle. Initial rearward movement of the slide by the physician causes the sheath to retract over the fixed basket tube, exposing the basket member and permitting it to open. Further rearward movement of the slide by the physician brings the slide into driving engagement with the piston. Thereafter, subsequent movement of the slide displaces the piston to exert a tension on the control wire to expand the basket member.

In a second embodiment the sheath is fixedly mounted to the forward end of the handle. The rearward end of the basket tube is mounted to the thumb slide, and the rearward end of the control wire is attached to the piston. The thumb slide includes an arm which extends behind the piston, and a spring is interposed between the arm and the piston to bias the piston against the rearward end of the thumb slide. The physician advances the thumb slide to extend the basket tube and expose the basket, permitting the basket to open. The piston with control wire is drawn along with the thumb slide until the piston confronts a stop member. Thereafter the thumb slide can be advanced without advancing the piston, thus extending the basket tube toward the tip of the basket assembly and expanding the basket.

Thus it is an object of the present invention to provide an improved stone basket for removing stones from the urinary system of a human patient.

It is another object of the present invention to provide a stone basket in which both the sheath and the center wire can be manipulated without the physician having to move his finger between two slides.

Another object of the present invention is to provide an improved stone basket which does not distract the physician by diverting his attention to locating a particular slide to manipulate the device.

It is still another object of the present invention to provide a stone basket which minimizes the possibility of inadvertently breaking the center wire.

A further object of the present invention is to provide an improved stone basket which prevents the physician from exerting a tension on the center wire while the basket is still encased within its sheath.

Other objects, features, and advantages of the present invention will become apparent upon reading the following specification, when taken in conjunction with the drawings and the appended claims.

BRIEF DESCRIPTION OF THE DRAWINGS

FIG. 2A is a side view of a handle of the stone basket of FIG. 1; FIG. 2B is a top view of the handle of FIG. 2A; FIG. 2C is a front view of the handle of FIG. 2A; FIG. 2D is a partial bottom view showing the nose of the handle of FIG. 2A; and FIG. 2E is a perspective view of the handle of FIG. 2A.

FIG. 6A is a side view of a thumb slide of the stone basket of FIG. 1; FIG. 6B is a front view of the thumb slide of FIG. 6A; and FIG. 6C is a perspective view of the handle of FIG. 6A.

FIG. 7A is a side view of a piston of the stone basket of FIG. 1; FIG. 7B is a perspective view of the piston of FIG. 7A.

FIG. 11A is a side view of the stone basket of FIG. 10 partially cut away to reveal interior detail and showing the basket in its retracted position; FIG. 11B is a side view of the stone basket of FIG. 10 partially cut away to reveal interior detail and showing the basket in an open position; and FIG. 11C is a side view of the stone basket of FIG. 10 partially cut away to reveal interior detail and showing the basket in an expanded position.

DETAILED DESCRIPTION OF THE DISCLOSED EMBODIMENT

Figure 1:
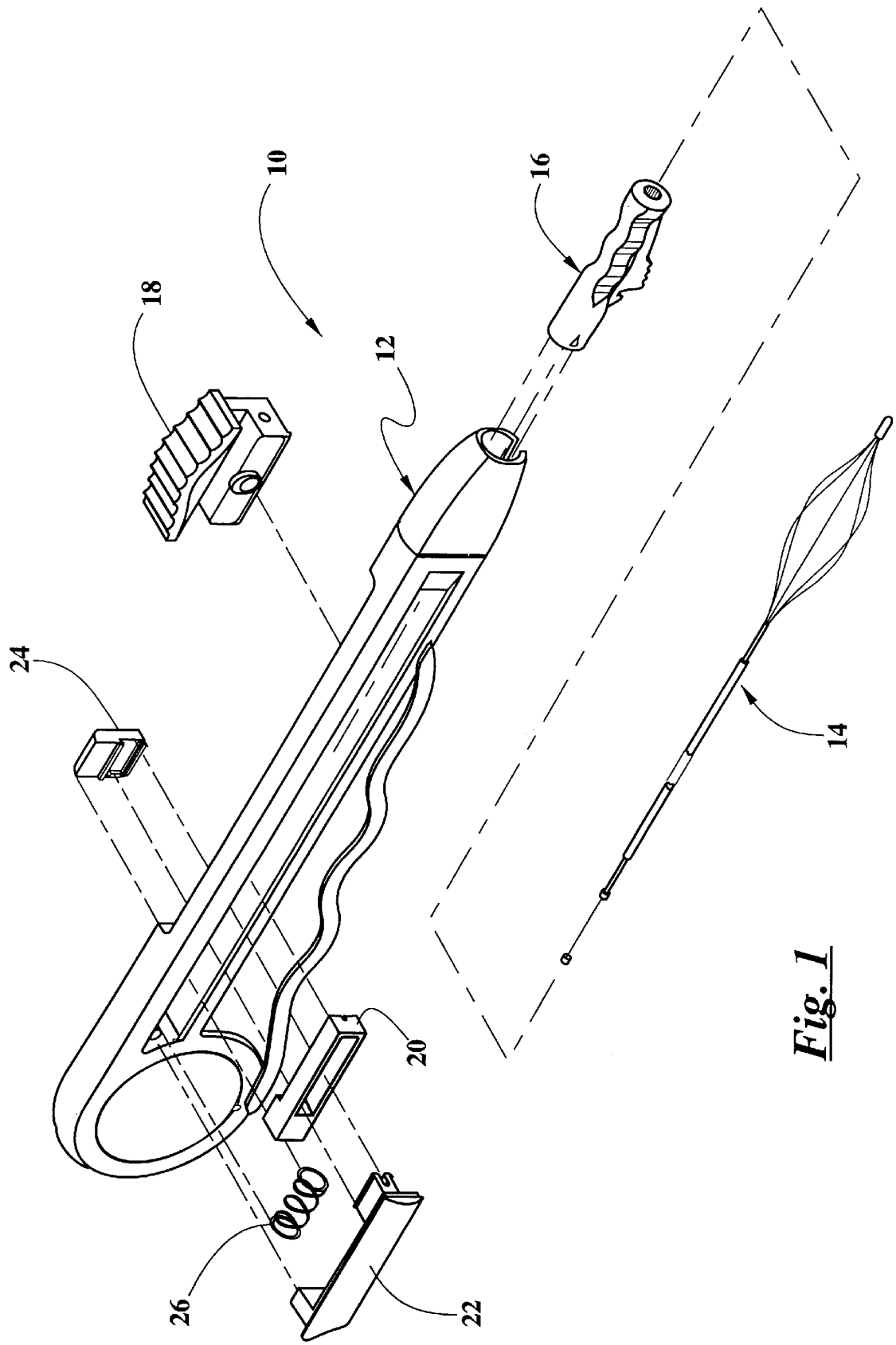
FIG. 1 is an exploded isometric view of a first embodiment of a stone basket according to the present invention.

Referring now in more detail to the drawings in which like numerals indicate like elements throughout the several views, FIG. 1 is an exploded view of an improved stone basket 10 according to the present invention. The stone basket 10 consists of a number of subcomponents: a handle 12, a basket assembly 14, a luer clip 16, a thumb slide 18, a piston 20, a right retainer 22, a left retainer 24, and a coil spring 26. Each of these subcomponents will now be described in more detail.

Referring now to FIG. 2, the handle 12 functions as the frame to which the other subcomponents are mounted. The handle 12 has a rounded back end 30 and a tapered forward end 32. A grip portion 34 curved to accept the fingers of a physician is formed at the bottom edge of the handle.

As can be seen in FIGS. 2B and 2D, the central upper portion of the handle 12 has a recess 38 formed in the left side, forming a narrow spine 40 running along the top of the handle. Just below the spine 40, an elongated slot 42 is formed through the handle 12. The lower edge of the slot 42 lies in the same horizontal plane as the lower edge of the recess 38 so as to form a track 44 extending the width of the handle 12.

On the right side of the handle 12 rearward of the slot 42 is a hollow 46. A laterally extending pin 48 is located within the hollow 46.

A bore 50 extends through the nose 32 of the handle 12 parallel to the longitudinal axis of the handle. The rearward end of the bore 50 opens into the slot 42. A vertical notch 52 is formed in the lower edge of the nose 32 at its forward end in communication with the bore 50. As can be seen in FIG. 2D, a transverse rail 54 extends across the notch 52 adjacent its rearward end.

Figure 3A:
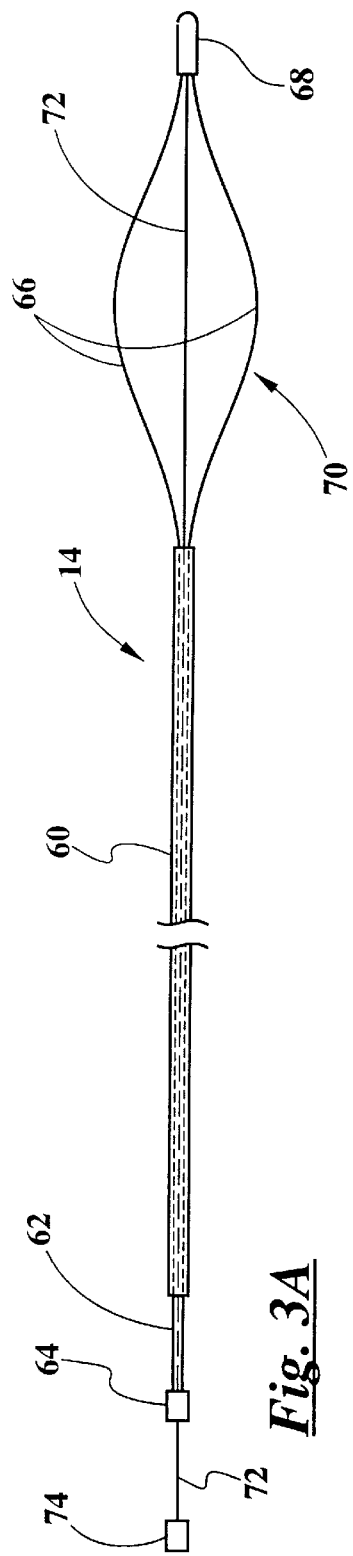
FIG. 3A is a side view of a basket assembly of the stone basket of FIG. 1 showing the basket in an open configuration.
Figure 3B:
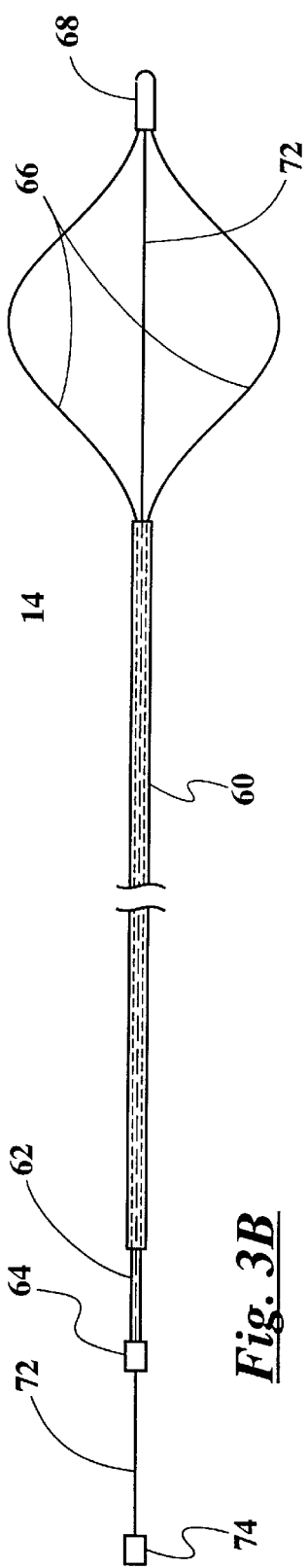
FIG. 3B is a side view of the basket assembly of FIG. 3A showing the basket in an expanded configuration.
Figure 3C:
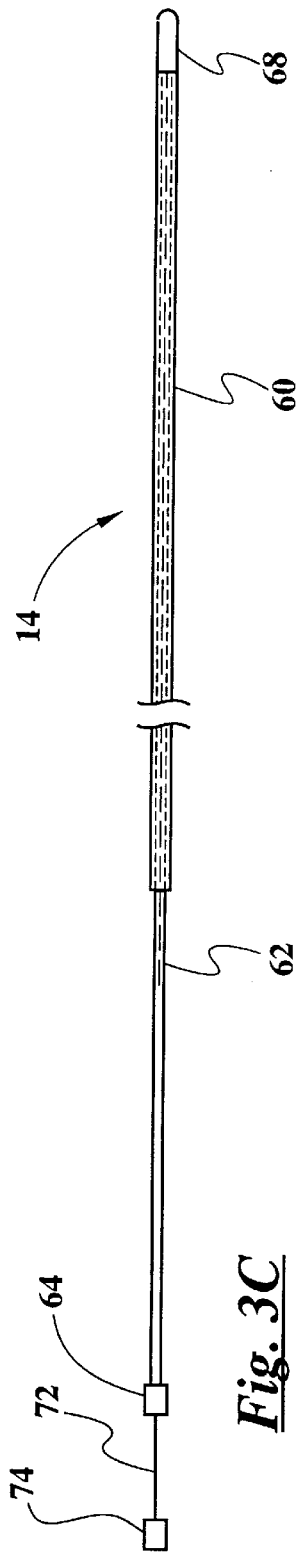
FIG. 3C is a side view of the basket assembly of FIG. 3A showing the basket retracted within its sheath.
Figure 4A:
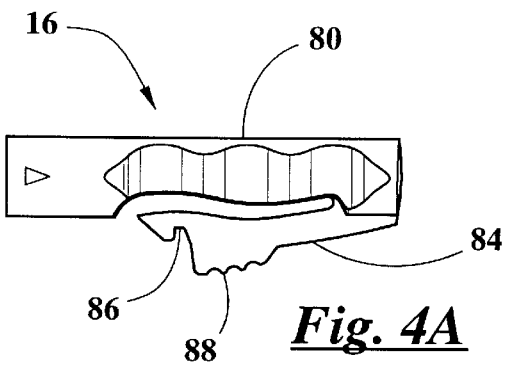
FIG. 4A is a side view of a luer clip of the stone basket of FIG. 1.
Figure 4C:
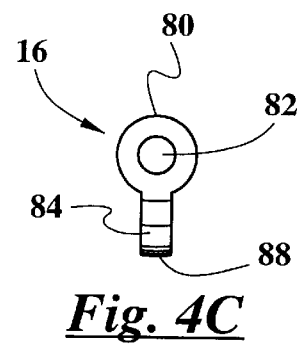
FIG. 4C is a front view of the luer clip of FIG. 4A.
Figure 4B:
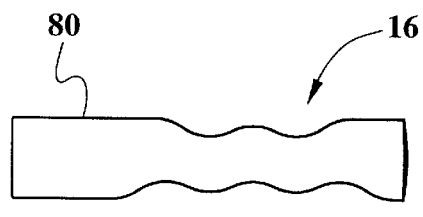
FIG. 4B is a top view of the luer clip of FIG. 4A.
Figure 4D:
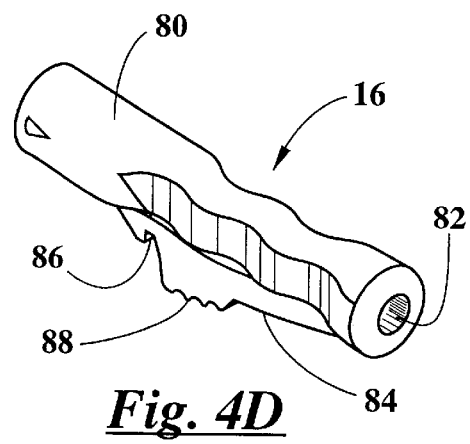
FIG. 4D is a perspective view of the luer clip of FIG. 4A.
Figure 4E:
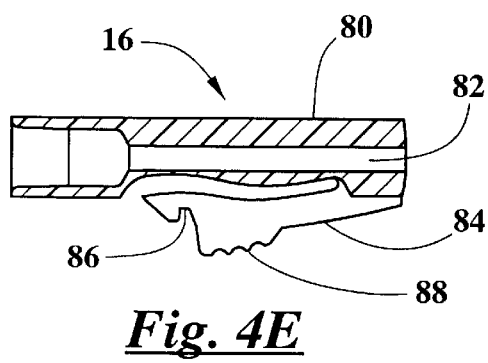
FIG. 4E is a side cutaway view of the luer clip of FIG. 4A.

Referring now to FIGS. 3A–3C, the basket assembly 14 has an outer sheath 60. A basket tube 62 is telescopically disposed within the sheath 60. A ferrule 64 is attached to the back end of the basket tube 62. The back ends of a plurality of basket wires 66 are anchored to the forward end of the basket tube 62. The forward ends of the basket wires 66 are connected to a tip 68. The basket wires 66 are comprised of a shape memory metal and bow outward. In combination, the bowed basket wires comprise a basket 70.

Slidably disposed within the basket tube 62 is a central control wire 72. The forward end of the control wire 72 is anchored to the tip 68 of the basket assembly 14. The control wire 72 runs the length of the basket tube 62 and extends from its rear end. A ferrule 74 is attached to the rearward end of the control wire 72.

The basket assembly 14 operates in a generally conventional manner. Referrring first to FIG. 3A, the sheath 60 is retracted (moved toward the left, as seen in FIG. 3A) to expose the basket 70. With the sheath 60 exposed, the basket wires 66 bow outward to open the basket 70. When a tension is exerted on the control wire 72 as shown in FIG. 3B (i.e., the control wire is pulled toward the left as seen in FIG. 3B), the tip 68 of the basket assembly 14 is drawn toward the forward end of the basket tube 62. As the distance between the tip 68 and the basket tube 62 decreases, the basket wires 66 are bowed outward to expand the basket, as shown in FIG. 3B.

FIG. 3C shows the basket assembly 14 with the sheath 60 fully extended to cover the basket 70.

Referring now to FIGS. 4A–4E, the luer clip 16 includes a body portion 80 having a longitudinal bore 82. The bore 82 is of sufficient diameter to permit the sheath 60 of the basket assembly 14 to slide freely therein. A cantilevered spring arm 84 extends downward and rearward from the lower front edge of the luer clip 16. A notch 86 is formed adjacent the free end of the spring arm 84. A series of ribs 88 is formed on the lower edge of the spring arm 84 to provide a grip surface.

Figure 5A:
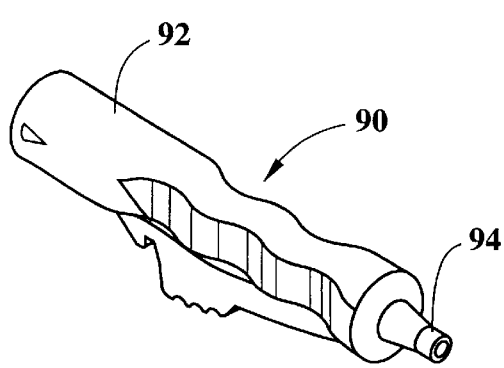
FIG. 5A is a perspective view of an alternate embodiment of a luer clip.
Figure 5B:
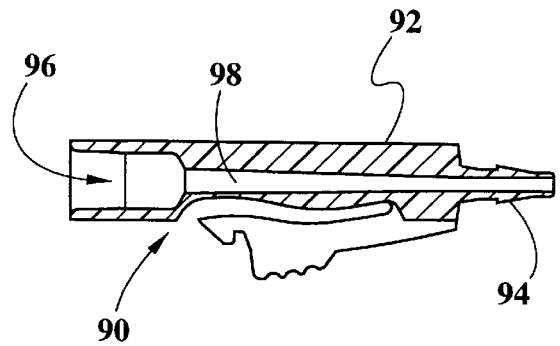
FIG. 5B is a side cutaway view of the luer clip of FIG. 5A.
Figure 8A:
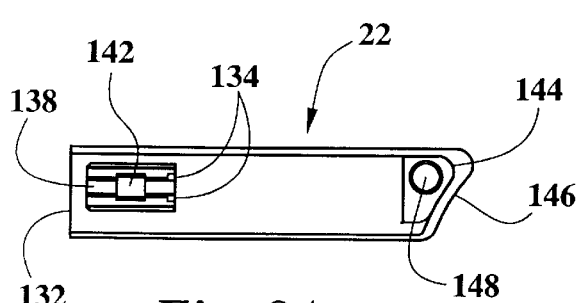
FIG. 8A is a side view of a right retainer of the stone basket of FIG. 1.
Figure 8B:
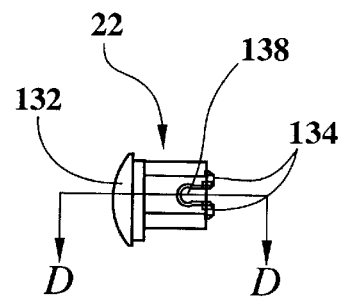
FIG. 8B is an end view of the right retainer of FIG. 8A.
Figure 8C:
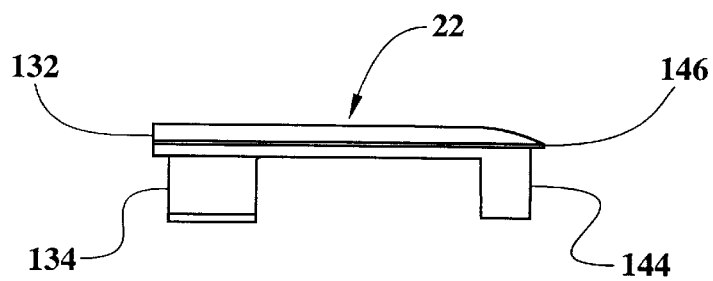
FIG. 8C is a top view of the right retainer of FIG. 8A.
Figure 8D:
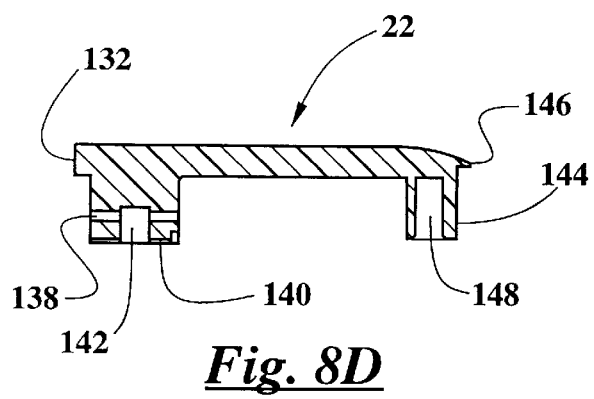
FIG. 8D is a cutaway view as seen along line D—D of FIG. 8B.
Figure 8E:
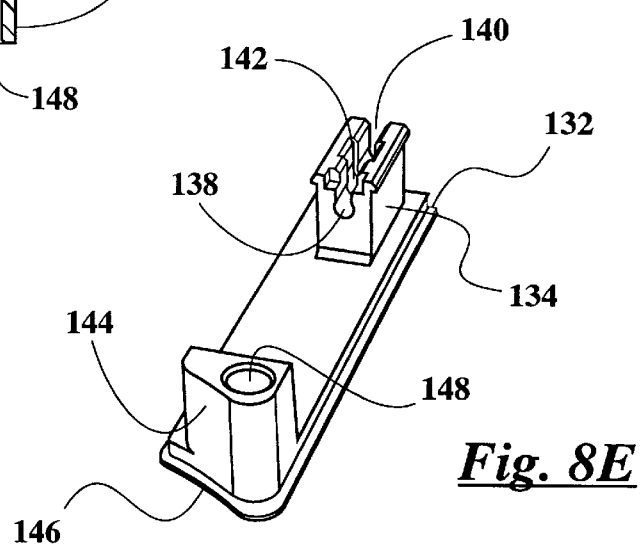
FIG. 8E is a perspective view of the right retainer of FIG. 8A.
Figure 9A:
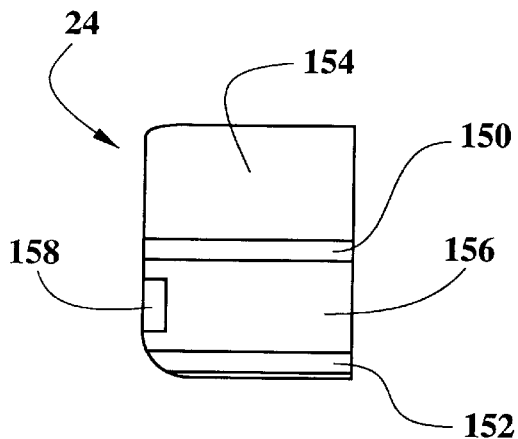
FIG. 9A is a side view of a left retainer of the stone basket of FIG. 1.
Figure 9B:
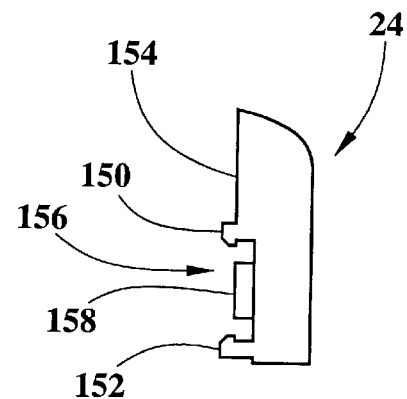
FIG. 9B is a top view of the left retainer of FIG. 9A.
Figure 9C:
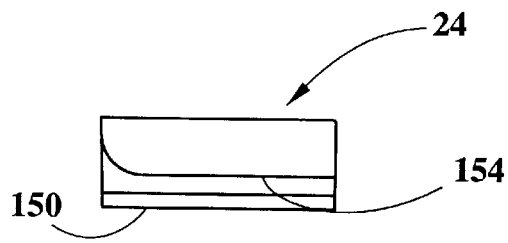
FIG. 9C is a front view of the left retainer of FIG. 9A.
Figure 9D:
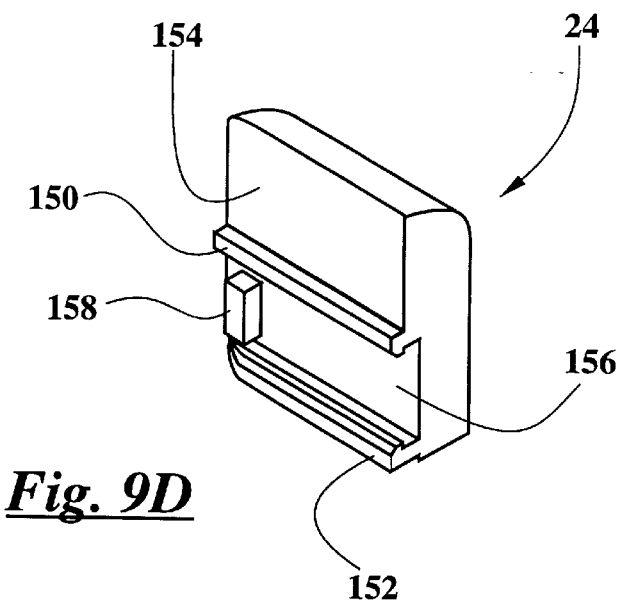
FIG. 9D is a perspective view of the left retainer of FIG. 9A.

An alternate embodiment of a luer clip 90 is illustrated in FIGS. 5A and 5B. The luer clip 90 of the alternate embodiment includes a body portion 92. A nipple 94 is formed at the forward end of the body portion 92. The nipple 94 is configured such that the rearward end of a sheath 60 of a basket assembly 14 can fit onto its forward end. A luer recess 96 is formed in the rearward end of the body portion 92. A tapered longitudinal bore 98 is formed within the body portion 92 and extends from the luer recess 96 to through the nipple 94. Thus a hypodermic syringe which is coupled to the luer clip 16 by way of the luer recess 96 can infuse a fluid through the longitudinal bore 98 and into a sheath attached to the nipple 94. More details regarding the purpose and function of the luer clip 90 of the alternate embodiment will be explained below in conjunction with a discussion of a second embodiment of a stone basket.

The thumb slide 18 comprises a body portion 100 which is dimensioned to be received within the slot 42 of the handle 12. A downward extending flange 102 is formed along the right side of the body portion 100. A tab 104 extends upward from the right side of the body portion 100. A longitudinal bore 106 extends through the body portion 100 parallel to its longitudinal axis. A transverse bore 108 extends from the left side of the body portion to the right side and intersects the longitudinal bore 106. A bracket 110 extends upward from the left side of the body portion 100. At the upper end of the bracket 110 a finger-receiving button 112 has a ribbed upper surface 114 to provide a non-slip grip.

The piston 20 is a generally box-shaped member dimensioned to slide within the slot 42 in the handle 12. The piston 20 is open along both sides. A semicircular recess 120 is formed in the front wall 122 of the piston 20 along the longitudinal axis of the piston. A cavity 124 is formed adjacent the rearward end 126 of the piston 20 and is dimensioned to receive the ferrule 74 of the control wire 72 (FIGS. 3A–3C). A notch 128 in communication with the cavity 124 is adapted to receive the control wire 72.

The right retainer 22 is an elongated panel configured to cover the hollow 46 in the right side of the handle 12 just rearward of the slot 42 (see FIGS. 2A–2E). Adjacent its forward end 132 the right retainer 22 has a pair of flanges 134 extending inward from its inner face 136 in parallel, spaced relation. The flanges 134 define a circular opening 138 which is open along one side 140. The free ends of the flanges 134 are tapered toward the opening 138 to facilitate introducing a wire therebetween. A cavity 142 in communication with the circular opening 138 is dimensioned to receive the ferrule 64 of the basket tube 62 therewithin (see FIGS. 3A–3C). A lobe 144 is formed on the inner face 136 of the right retainer 22 adjacent its rearward end 146. The lobe 144 has a circular bore 148 formed therein to receive the pin 48 on the handle 12.

The left retainer 24 is a panel configured to cover the rear portion of the recess 38 in the left side of the handle 12. Upper and lower flanges 150, 152 extending from the inner face 154 of the left retainer 24 define a channel 156 therebetween. The dimensions of the channel 156 are such as will receive the free ends of the flanges 134 of the right retainer 22 in an interference fit. A stop 158 is formed at the rearward end of the channel 156.

Figure 10:
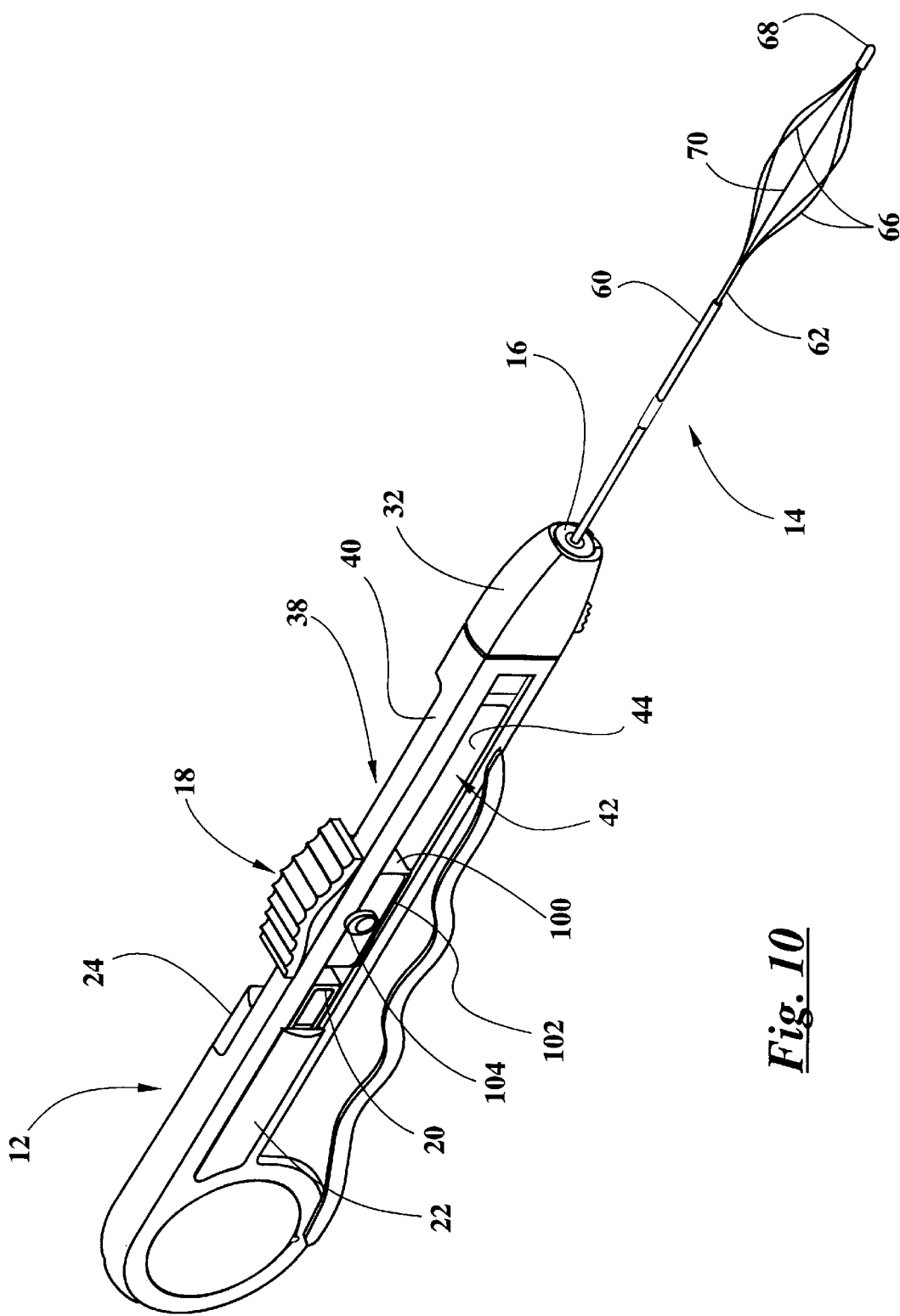
FIG. 10 is a perspective view of an assembled stone basket according to the first disclosed embodiment of the invention.

Assembly of the stone basket 10 will now be described. The rearward end of the luer clip 16 is inserted into the opening 50 in the nose 32 of the handle 12, with the spring arm 84 of the luer clip riding within the notch 52 in the underside of the nose. As the luer clip 16 is slid rearward, the beveled rearward edge of the spring arm 84 confronts the rail 54 which extends across the notch 52. Further rearward movement of the luer clip 16 biases the spring arm 84 upward until the notch 86 in the lower edge of the spring arm 84 snaps over the rail 54. The luer clip 16 is now secured in place in the handle 12, as shown in FIG. 10.

The basket assembly 14 is disassembled, and the rearward end of the sheath 60 is inserted into the forward end of the longitudinal bore 106 in the thumb slide 18. The rearward end of the sheath 60 is then secured to the thumb slide 18 in any suitable manner. In the disclosed embodiment, an epoxy adhesive is infused into the transverse bore 108 of the thumb slide 18 to adhesively bond the sheath 60 to the thumb slide.

The forward end of the sheath is now introduced through the rearward end of the longitudinal bore 82 of the luer clip 16. The sheath is advanced until the thumb slide 18 is is in register with the slot 42 in the handle 12. The right end of the body portion 100 is inserted through the slot 42 from the left side of the handle 12. The upward extending tab 104 and downward extending flange 102 extend above and below the slot, respectively, on the right side of the handle 12 to slidably capture the thumb slide 18 within the handle. The spine 40 of the handle 12 extends between the finger-receiving button 112 and the body portion 100 of the thumb slide 18, with the bracket 110 of the thumb slide being located on the left side of the spine of the handle as shown in FIG. 10.

The piston 20 and right retainer 22 are now mounted to the control wire 72 and basket tube 62 assembly. The ferrule 74 of the control wire 72 is inserted into the cavity 124 of the piston 20 and adhesively bonded in place. The control wire 72 is positioned within the notch 128 and semicircular recess 120 of the piston. The ferrule 64 of the basket tube 62 is then positioned within the cavity 142 defined by the flanges 134 on the inner face of the right retainer 22. In the disclosed embodiment the ferrule 64 is adhesively bonded within the cavity 142. The basket tube 62 is introduced into the open side 140 of the circular opening 138 between the flanges 134 of the right retainer and positioned within the circular opening.

With the piston 20 and right retainer 22 thus mounted to the basket tube 62 and control wire 72 assembly, the tip 68 at the forward end of the assembly is inserted through the back end of the longitudinal bore 106 in the thumb slide 18. When the control wire 72 and basket tube 62 have been advanced into the sheath 60, the piston 20 and right retainer 22 are mounted to the handle. The piston 20 is first positioned on the track 42 within the slot 42 of the handle 12 with the cavity 124 of the piston 20 facing the left side of the handle. The right retainer 22 with basket tube 62 mounted thereto is then assembled onto the handle 12. The pin 48 on the handle 12 is received snugly within the circular bore 148 formed in the lobe 144 of the right retainer 22. The flanges 134 of the right retainer are inserted through the open sides of the piston. The left retainer 24 is then assembled onto the handle 12 by means of the flanges 134 of the right retainer being received within the channel 156 on the inner face 154 of the left retainer in an interference fit. Assembly of the stone basket 10 is now complete.

Operation of the stone basket 10 will now be explained with respect to FIGS. 11A–C. Initially, as shown in FIG. 11A, the thumb slide 18 is placed in its forwardmost position so that the sheath 60 will be extended over the basket 70.

To open the stone basket 10, the physician retracts the thumb slide 18 rearward, as illustrated in FIG. 11B. The basket tube 62 is held in a stationary position relative to the handle 12 by way of the ferrule 64 of the basket tube 62 being captured between the flanges 134 of the right retainer 22. Retracting the thumb slide 18 draws the sheath 60 rearward. Since the basket tube 62 remains stationary, retracting the sheath 60 exposes the basket 70. As the basket 70 is uncovered, the basket wires 66 assume their shape memory position and bow outward, opening the basket. When the thumb slide 18 has been moved rearward sufficiently to retract the sheath 60 to expose the basket 70, the rearward end of the thumb slide body 100 contacts the forward end of the piston 20.

If the physician desires to expand the basket 70 further, he moves the thumb slide 18 further rearward. As can be seen in FIG. 11C, further movement of the thumb slide 18 displaces the piston 20 rearward. Since the control wire 72 is attached to the piston 20, a tension is exerted on the control wire. This tension draws the tip 68 of the basket assembly 14 toward the basket tube 62, causing the basket wires 66 to bow further outward. When rearward pressure on the thumb slide 18 is released, the spring 26, compressed by the rearward movement of the piston 20, biases the piston to its forward position. The physician can close the basket 70 to crush or capture a stone by sliding the thumb slide 18 forward, which advances the sheath 60 over the basket 70 and collapses the basket wires 66.

The stone basket 10 of the first embodiment of the present invention provides several advantages over conventional stone baskets. First, because both the sheath 60 and the control wire 72 are retracted by movement of the thumb slide 18, the physician does not need to move his finger from one slide to another. Thus the physician's attention is not diverted from positioning the basket.

Further, because the piston 20 cannot be retracted until the thumb slide 18 is moved sufficiently far rearward to retract the sheath 60, the control wire 72 cannot be tensioned while the sheath is extended. Thus the possibility is eliminated of the physician inadvertently breaking the control wire 72 by retracting it with the sheath 60 extended.

Figure 12A:
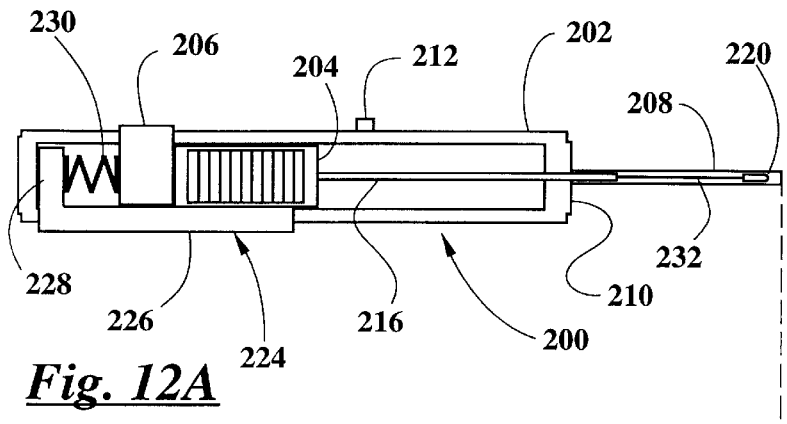
FIG. 12A is a schematic illustration of a second embodiment of a stone basket according to the present invention, showing the basket in a retracted position.
Figure 12B:
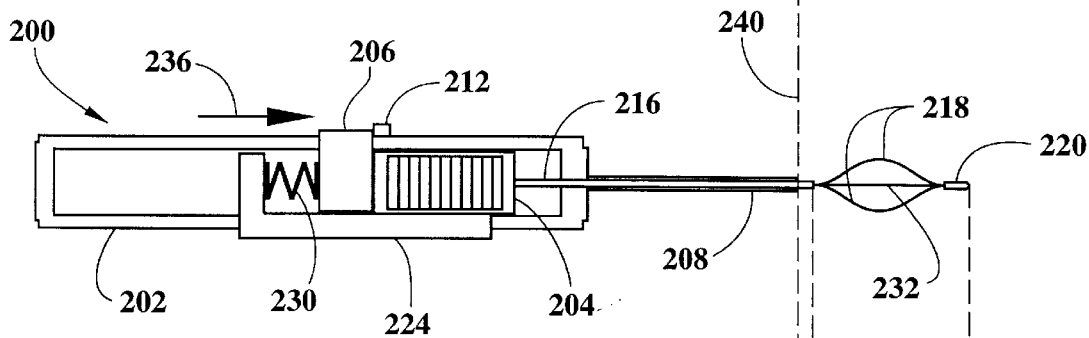
FIG. 12B is a schematic illustration of the stone basket of FIG. 12A showing the basket in an open position.
Figure 12C:
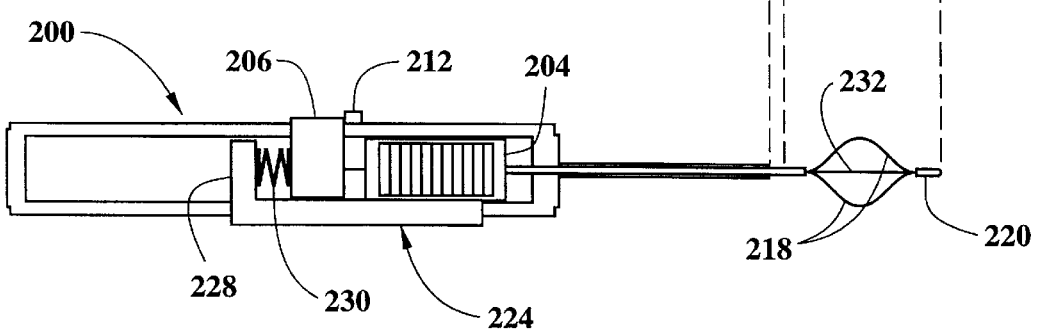
FIG. 12C is a schematic illustration of the stone basket of FIG. 12A showing the basket in an expanded position.

Referring now to FIGS. 12A–C, a second embodiment of a stone basket 200 is schematically illustrated. The stone basket 200 comprises a housing 202 to which a thumb slide 204 and piston 206 are slidably mounted. A sheath 208 is fixedly mounted to the forward end 210 of the housing 202. A stop 212 is formed on the housing 202 and extends into the sliding path of the piston 206 but not the thumb slide 204.

A basket tube 216 is telescopically received within the sheath 208. The rearward end of the basket tube 216 is fixedly mounted to the thumb slide 204. At the forward end of the basket tube 216, a plurality of basket wires 218 (FIG. 31) form a stone basket. The forward ends of the basket wires 218 are attached to a tip 220.

An arm 224 is attached to the thumb slide 204. The arm 224 is L-shaped and includes a rearward extending member 226 and a transverse member 228 which is located in space-apart relation to the piston 206. A coil spring 230 is located between the transverse section 228 of the arm 224 and the rearward end of the piston 206.

A control wire 232 is slidably disposed within the basket tube 216. The rearward end of the control wire 232 is attached to the piston 206, and the forward end of the control wire is attached to the tip 220.

In FIG. 12A, the thumb slide 204 and piston 206 are in their rearmost positions. The basket tube 216, basket wires 218, and tip 220, as well as the control wire 232, are all retracted within the sheath 208.

In FIG. 12B, the thumb slide 204 has been advanced to the position shown. The arm 224 attached to the thumb slide 204, acting through the spring 230, has pushed the piston 206 along with the thumb slide. In this position, the basket wires 218 have been extended beyond the forward end of the sheath 208, and the basket wires have assumed their expanded position. The piston 206 has confronted the stop 212 on the housing 202.

In FIG. 12C, the thumb slide 204 has been advanced further. The piston 206 is prevented from advancing further by the stop 212 on the housing 202. The spring 230 between the arm 224 and the piston 206 compresses as the thumb slide 204 advances. Because the piston 206 cannot advance, the control wire 232 remains fixed, and the tip 220 attached to the forward end of the control wire remains fixed. Thus as the thumb slide 204 advances, the forward end of the basket tube 216 moves toward the tip 220, causing the basket wires 218 to bow outward even further.

As the physician releases pressure on the thumb slide 204, the spring 230 pushes against the arm 224 and draws the thumb slide rearward. In this position, the back end of the thumb slide 204 bears against the front end of the piston 206. Thereafter, as the physician draws the thumb slide 204 rearward, the piston 206 is pushed rearward along with the thumb slide, retracting both the basket tube 216 and the center wire 232 simultaneously.

As will be understood from the foregoing explanation, the stone basket 200 of the second embodiment differs from the stone basket 10 of the first embodiment in two primary respects. First, the thumb slide 204 of the instrument 200 is advanced to open the basket, whereas the thumb slide 14 of the instrument 10 is retracted to open the basket. Second, the sheath 208 of the stone basket 200 is fixed with the control wire 232 and basket tube 216 being movable to open the basket, whereas in the stone basket 10 the basket tube 62 is fixed, with the sheath 60 and a control wire 72 being movable to open the basket. However, both designs 10, 200 share the feature that actuation of a single thumb slide will both open the basket and expand the basket beyond its normal open configuration. In addition to the advantage of the physician having to operate only a single slide, this arrangement also provides the advantage that the control wire and basket tube cannot be moved relative to one another while the basket is retracted within the sheath. Thus the possibility of the physician attempting to expand the basket while the basket is still enclosed within the sheath, and thereby possibly breaking the control wire, is eliminated.

The stone basket 200 of the second embodiment provides the further advantage that the sheath 208 can be fixedly mounted to a luer clip 90. Should it become necessary to infuse a fluid into the patient, the luer clip 90 can be quickly removed from the handle 12 by depressing the spring arm 84 to disengage it from the rail 54 in the nose 32 of the handle. The basket tube 216 and control wire 232 can be quickly withdrawn from the rearward end of the sheath 208, and a syringe can be coupled to the rear end of the luer clip 90. Fluid can be infused from the syringe, through the luer clip 90, and through the sheath 208.

Variations of stone basket 200 will be readily apparent to those skilled in the art. For example, the stone basket 200 has been disclosed with respect to an arm 224 mounted to the thumb slide 204 which extends behind the piston 206 and permits use of a coil spring 230 which is compressed when the piston confronts the stop 212. However, an acceptable alternative is a coil spring which is interposed between the thumb slide 204 and the piston 206 and which is attached to both members. Advancing the thumb slide 204 will exert a tension on the spring which will draw the piston 206 forward. When the piston 206 confronts the stop 212, the piston will cease forward movement, and the spring will stretch to permits further forward movement of the thumb slide 204. Both arrangements provide a means for biasing the piston forward as the thumb slide is advanced.

Also, while the foregoing embodiments have been disclosed with respect to a basket assembly in which the basket is mounted to the forward end of a basket tube, it will be appreciated that any suitable shaft can be used, and that the invention is not limited to a tubular shaft for the basket.

Finally, it will be understood that the preferred embodiment has been disclosed by way of example, and that other modifications may occur to those skilled in the art without departing from the scope and spirit of the appended claims.

What is claimed is:

1. A stone basket comprising:

a handle;

a slide movably mounted to said handle and operable from outside said handle, said slide being movable between a first slide position and a second slide position;

a piston movably mounted to said handle for movement between a first piston position and a second piston position;

a basket shaft having proximal and distal ends, said basket shaft having an expandable basket member adjacent its proximal end, said distal end of said basket shaft being mounted to said handle;

a sheath extending over said basket shaft and having proximal and distal ends, said distal end of said sheath being attached to said slide, said expandable basket member being enclosed within said proximal end of said sheath when said slide is in said first slide position, and said sheath being retracted to expose said expandable basket member when said slide is in said second slide position;

a control wire extending along said basket shaft and having proximal and distal ends, said distal end of said control wire being attached to said piston, and said proximal end of said control wire being attached adjacent a forward portion of said expandable basket such that moving said piston from said first piston position to said second piston position exerts a tension on said control wire which causes said expandable basket member to expand;

said slide in said first slide position being drivably disengaged from said piston; and said slide and said piston being configured such that said movement of said slide to said second slide position brings said slide into driving engagement with said piston, such that movement of said slide from said second slide position to a third slide position moves said piston from said first piston position to said second piston position;

whereby movement of said slide from said first slide position to said second slide position retracts said sheath to expose said basket member, and whereby further movement of said slide from said second slide position to said third slide position exerts a tension on said control wire to expand said basket member.

2. The stone basket of claim 1, wherein said piston is substantially inaccessible to a user from outside said housing such that said piston can be actuated only by movement of said slide.

3. The stone basket of claim 1, wherein said basket shaft comprises an elongated tube, and wherein said control wire extending along said basket shaft comprises said control wire extending through said tube.

4. A stone basket comprising:

a handle having forward and rearward ends;

a slide movably mounted to said handle and operable from outside said handle, said slide being movable between a first slide position and a second slide position forward of said first slide position;

a piston movably mounted to said handle rearward of said slide;

means operatively associated with said slide and said piston for biasing said piston forward as said slide is advanced and for permitting at least limited movement of said slide upon forward movement of said piston being limited;

means operatively associated with said handle for limiting forward movement of said piston a basket shaft having proximal and distal ends, said basket shaft having an expandable basket member adjacent its proximal end, said distal end of said basket shaft being mounted to said slide;

a sheath extending over said basket shaft and having proximal and distal ends, said distal end of said sheath being attached to said handle, said expandable basket member of said stone basket being enclosed within said proximal end of said sheath when said slide is in said first slide position, and said basket shaft being extended to expose said expandable basket member when said slide is in said second slide position;

a control wire extending along said basket shaft and having proximal and distal ends, said distal end of said control wire being attached to said piston, and said proximal end of said control wire being attached adjacent a forward portion of said expandable basket;

said slide and said piston being configured such that said movement of said slide to said second slide position brings said piston into engagement with said forward movement limiting means, such that movement of said slide from said second slide position to a third slide position forward of said second slide position advances said slide without advancing said piston;

whereby movement of said slide from said first slide position to said second slide position extends said basket assembly to expose said basket member, and whereby further movement of said slide from said second slide position to said third slide position moves said basket member relative to said control wire to expand said basket member.

5. The stone basket of claim 4, wherein said piston is substantially inaccessible to a user from outside said housing such that said piston can be actuated only by movement of said slide.

6. The stone basket of claim 4, wherein said basket shaft comprises an elongated tube, and wherein said control wire extending along said basket shaft comprises said control wire extending through said tube.

* * * * *